United States Patent [19]

Thomas et al.

[11] 4,381,008
[45] Apr. 26, 1983

[54] METHODS OF IMPROVING SURFACE CHARACTERISTICS OF EXTRUDED THERMOPLASTIC TUBING AND PRODUCTS PRODUCED THEREBY

[75] Inventors: Joseph J. Thomas, Bridgewater; Martin Sobel, Flemington, both of N.J.

[73] Assignee: Johnson & Johnson, New Brunswick, N.J.

[21] Appl. No.: 940,548

[22] Filed: Sep. 8, 1978

[51] Int. Cl.³ .................................................. A61M 25/00
[52] U.S. Cl. ......................................................... 604/265
[58] Field of Search ................... 128/214 R, 348, 349; 264/290 R, 294, 231; 29/458

[56] References Cited

U.S. PATENT DOCUMENTS

| | | | |
|---|---|---|---|
| 3,148,369 | 5/1965 | Haseley | 264/290 R |
| 3,225,762 | 12/1965 | Guttman | 128/348 |
| 3,681,483 | 8/1972 | Moore | 264/294 |
| 3,877,429 | 4/1975 | Rasumoff | 128/221 |
| 3,898,993 | 8/1975 | Taniguchi | 128/348 |
| 4,119,094 | 10/1978 | Micklus et al. | 128/348 |

FOREIGN PATENT DOCUMENTS

| | | | |
|---|---|---|---|
| 4998478 | 9/1974 | Japan | 264/294 |
| 1216176 | 12/1970 | United Kingdom | 264/231 |

*Primary Examiner*—Richard J. Apley
*Assistant Examiner*—T. J. Wallen

*Attorney, Agent, or Firm*—Donal B. Tobin

[57] ABSTRACT

A method of improving the surface lubricity of extruded thermoplastic tubing for inclusion in medical devices wherein the tubing is intended for insertion into the human body includes providing a finite section of hollow extruded thermoplastic tubing which has been cooled to room temperature following an extrusion process. The tubing has a first lubricity level on its outer surface. The method steps further include maintaining the tubing substantially at room temperature conditions and applying a longitudinal stretching force to the tubing sufficient to exceed the elastic limit of the tubing whereby the tubing is deformed from its original dimensions. This stretching produces a second lubricity level on the outer surface of the tubing which is an improvement over the first lubricity level so that the tubing may slide more clearly and with less friction during insertion.

This method of improving the surface characteristics of extruded thermoplastic tubing is adaptable to a method of fabricating an intravenous catheter assembly wherein a section of extruded thermoplastic tubing is connected to a hub which serves as a connection device for delivering solutions to a patient. The tubing may be stretched either before or after its insertion into the hub. As a result of this stretching, the surface lubricity of the tubing is improved to allow it to slide more freely during intravenous insertion.

2 Claims, 7 Drawing Figures

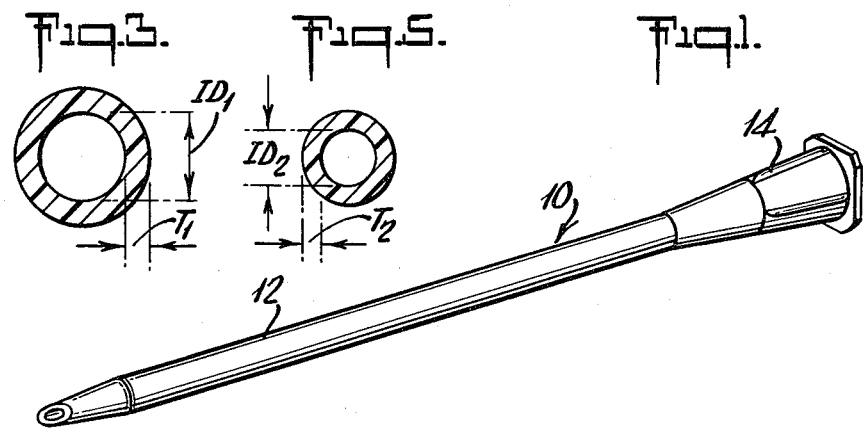
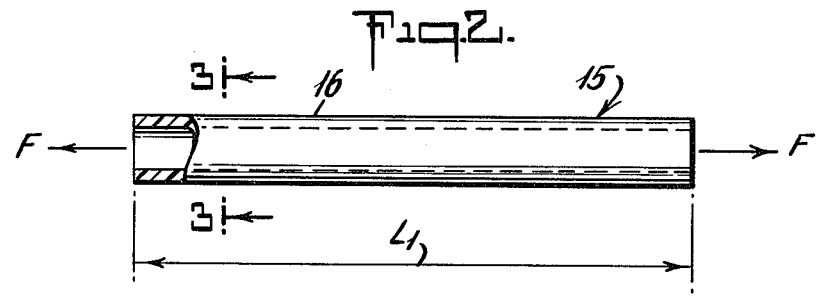
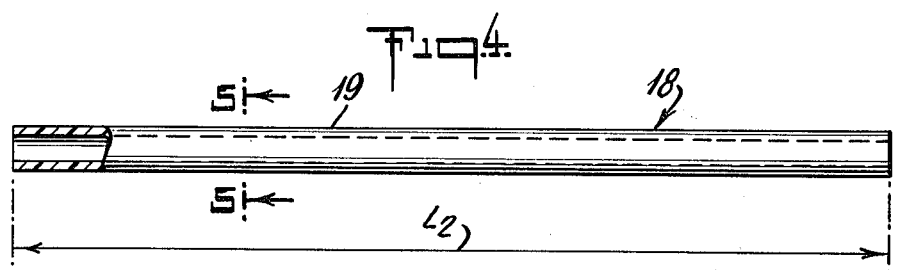
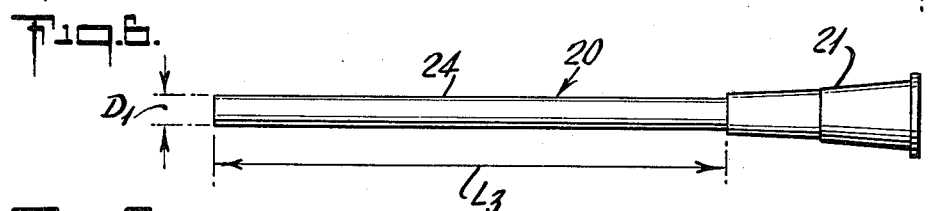
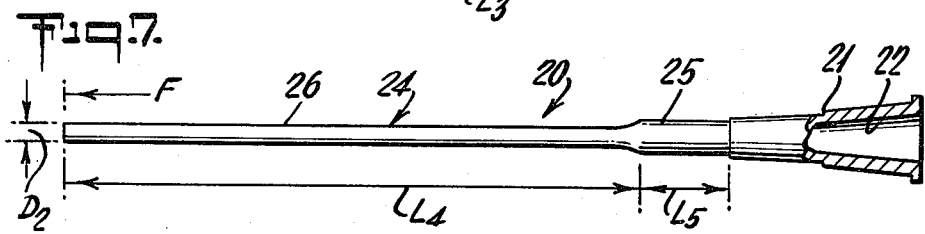

METHODS OF IMPROVING SURFACE CHARACTERISTICS OF EXTRUDED THERMOPLASTIC TUBING AND PRODUCTS PRODUCED THEREBY

BACKGROUND OF THE INVENTION

This invention relates to methods of improving surface characteristics of extruded thermoplastic tubing, particularly such tubing for inclusion in medical devices in which the tubing is intended for intravascular insertion into the human body.

Tubular products which are intended for medical applications, and more specifically, which are to be introduced into the body making contact with body tissue, fluids or vessels are preferably made as smooth as possible in order to minimize friction and drag during bodily insertion. Most plastic tubular products, suitable for catheters and the like, are formed by an extrusion process so that the outside surface of the tubing has relatively smooth properties. In many instances, a standard extrusion process for producing hollow tubular plastic products can be optimized to produce a lubricity level on the outside surface of the tubing which is adequate for medical purposes. However, although this surface lubricity or smoothness may be acceptable from the operational standpoint, the level of surface smoothness produced by mere extrusion may still produce some discomforturn to the patient because of surface friction and drag during insertion.

Some efforts have been taken to improve surface lubricity of extruded thermoplastic tubing by applying silicone fluids or resins thereon. This, however, requires an additional operational step and increases expense of the product. Furthermore, cleanliness and possible contamination have to be considered inasmuch as the tube is intended for bodily insertion. Accordingly, improved techniques are still being sought for improving the surface characteristics of extruded thermoplastic tubing intended for medical purposes.

In U.S. Pat. Nos. 3,205,290; 3,108,851; and 3,089,187, plastic tubing is extruded and then stretched. The purpose of the stretching is to molecularly orient the material in order to increase its strength in either the longitudinal or transverse directions. In these patents, the stretching operation is part of or immediately following the extrusion step so that the plastic material is generally at an elevated temperature. There is no indication in these patents that the stretching, which causes molecular re-orientation, also produces an increase in smoothness or surface lubricity of the tubular product.

SUMMARY OF THE INVENTION

The present invention includes a method of preparing extruded thermoplastic tubing for inclusion in medical devices in which the tubing is intended for insertion into the human body. The method steps include providing a finite section of hollow extruded thermoplastic tubing having a relatively smooth outer surface, a first wall thickness, a first inside diameter and a first length. The tubing is maintained at a temperature below its melting point, and a longitudinal stretching force is applied to the tubing sufficient to exceed the elastic limit of the tubing. A second wall thickness, a second inside diameter and a second length of tubing are produced. Both of second wall thickness and inside diameter are less than the respective first wall thickness and inside diameter, and the second length is greater than the first length. As a result of the stretching, the smoothness of the outer surface of the stretched tubing is improved over the smoothness of the original section.

Another aspect of the present invention includes a method of improving the surface lubricity of extruded thermoplastic tubing for inclusion in medical devices in which the tubing is intended for intravascular insertion into the human body. This method includes providing a finite section of hollow extruded thermoplastic tubing which has been cooled to room temperature following an extrusion process. The extruded tubing has a first lubricity level on its outer surface. While maintaining the tubing substantially at room temperature conditions, a longitudinal stretching force is applied to the tubing sufficient to exceed its elastic limit so that the tubing is deformed from its original dimensions. As a result of this stretching, a second lubricity level on the outer surface of the tubing is produced. This second level is an improvement over the first lubricity level so that the tubing may slide more freely and with less friction during intravascular insertion.

One utilization of the extruded thermoplastic tubing which is stretched in post-extrusion operation is its inclusion in an intravenous catheter assembly. The catheter assembly includes a section of hollow extruded thermoplastic tubing which is connected to a hub, serving as a connection means for delivering parenteral solution to a patient. The tubing may be stretched either before or after it is inserted into the hub. This stretching improves the surface characteristics of the extruded thermoplastic tubing and allows the same to slide more freely and with less friction during intravenous insertion.

A further aspect of the present invention relates to an intravenous catheter including a hub and a section of hollow extruded thermoplastic tubing connected to the hub and extending substantially axially therefrom. A first portion of the tubing adjacent the hub has a first surface lubricity, while a second portion of the tubing has a second surface lubricity. The second surface lubricity is an improvement over the first surface lubricity so that the second portion of the tubing may slide more freely and with less friction during intravenous insertion.

The methods of the present invention are notably different from prior art methods in which extruded thermoplastic tubing is stretched. In the present invention, the stretching is not part of the extrusion process, but is a post-extrusion operation. In other words, following the standard and known extrusion procedures, the tubing is allowed to cool to room temperature; then, either at room temperatures or following application of small amounts of heat to slightly heat the tubing, the force is applied to the tubing to stretch it and thereby not only change and deform the tubing to the desired dimensions, but also affect and improve the outside surface lubricity of the tubing.

In accordance with the principles of this invention, the method of stretching the section of extruded tubing somewhat surprisingly produces improved smoothness properties on the outside surface of the tubing. Thus, a relatively smooth surfaced tubing produced by the extrusion process is then further improved to produce greater lubricity by this post-extrusion operation. Another advantage of the present invention is the reduction of friction on the tubing which is inserted, for example, into a vein of a patient. The improved levels of lubricity on the outside surface of the tubing provides freer sliding and ease of insertion of the tubing into the patient.

A further advantage of the present invention is the elimination of additaments such as silicone fluids or resins to the tubing which heretofore have been used to produce increased lubricity of the tubing. Now, and as a result of the post-extrusion process of the present invention, the surface properties of the tubing are inherently increased without the need for added lubricating materials.

BRIEF DESCRIPTION OF THE DRAWINGS

FIG. 1 is a perspective view of an intravenous catheter assembly which typically includes extruded thermoplastic tubing and which is improved according to the methods of the present invention;

FIG. 2 is a plan view of a finite section of thermoplastic tubing following a standard extrusion process;

FIG. 3 is a cross-sectional view taken along line 3—3 of FIG. 2;

FIG. 4 is a plan view illustrating the section of tubing of FIG. 2 after it has been stretched under the post-extrusion stretching operation, thereby having a different length, inside diameter and wall thickness;

FIG. 5 is a cross-sectional view taken along line 5—5 of FIG. 4;

FIG. 6 is a plan view of an intravenous catheter, partially cut away, which includes thermoplastic tubing which has not been stretched; and FIG. 7 is a plan view of the embodiment of FIG. 6 illustrating an alternate structure of the tubing after it has been stretched according to the invention.

DETAILED DESCRIPTION

While this invention is satisfied by embodiments in many different forms, there is shown in the drawings and will herein be described in detail, preferred embodiments of the invention, with the understanding that the present disclosure is to be considered as exemplary of the principles of the invention and is not intended to limit the invention to the embodiments illustrated. The scope of the invention will be pointed out in the appended claims.

Extruded thermoplastic tubing is often included in products such as an intravenous catheter assembly 10 illustrated in FIG. 1. This intravenous catheter assembly includes two basic components, a section of extruded tubing 12 which is inserted into a generally plastic hub 14. Hub 14 serves as a connection device so that an IV line may be connected for delivering parenteral solution to a patient. This type catheter device is intended for insertion particularly into a blood vessel of a patient, but may also be introduced into other sections of the body for various purposes. It can be appreciated that minimized drag on the outside surface of tubing 12 is desirable to lessen any discomfiture which may be attendant to inserting the tubing into the patient.

Extruded thermoplastic tubing, such as polytetrafluorethylene; fluorinated ethylene—propylene (FEP); and particularly, barium sulfate filled FEP tubing, and similar tubing materials, may be produced with a relatively smooth outside surface. The operative steps of the extrusion can be adjusted to optimize the surface properties of the tubing which is being produced. To further improve the smoothness and lubricity properties on the outside surface of such tubing, a finite section of the extruded thermoplastic tubing 15 is provided as illustrated in FIG. 2. Tubing 15 has a first lubricity level on its outside surface 16. Lubricity may be measured by various techniques, but one approach is to pass the tubing through a control material, and measure the force required to make such insertion. The force required to advance the tubing through the material is a measure of the friction between the outside surface of the tubing and the control material. In addition, tubing 15 has a first length $L_1$, a first inside diameter $ID_1$ and a first wall thickness $T_1$, as illustrated in FIGS. 2 and 3. Moreover, this section of extruded tubing can be provided long after the extrusion process in which it was formed, and may, for example, be a shelf item, stored at commonly recognized room temperatures. In tubing 15, both wall thickness $T_1$ and inside diameter $ID_1$ are larger than desired for the final section of tubing following the stretching operation.

Preferably at room temperature such as between 50° F. and 80° F. (10° C. to 26° C.), but necessarily less than the melting point of the thermoplastic tubing, which in the case of barium sulfate filled FEP is approximately 487°–540° F. (253°–282° C.), tubing 15 is subjected to a longitudinal stretching force, designated by the latter "F" as seen in FIG. 2. This stretching force may be applied in various ways; including, for example, a pair of grips at opposite ends of the tubing which are operable to apply a tensile load to the tubing. The movement speed of the grips can be controlled, and the applied force monitored. Force F places tubing 15 under tensile stress along its longitudinal axis. A sufficient amount of stretching force F is applied to tubing 15 so that the elastic limit of the tubing is exceeded. Accordingly, that amount of force will produce a preferably applied to tubing 15 so that stretching can be uniform along the longitudinal length of the tubing. Furthermore, a small amount of heat may be applied in some instances to render the tubing more easily stretchable. Once the tubing has been stretched, this additional heat is removed so that the stretched tubing may cool down, once again, to room temperature.

FIGS. 4 and 5 illustrate the effect of the stretching force upon the extruded tubing. After force F is removed, stretched tubing 18 is produced. Stretched tubing 18 now has a second length $L_2$, which by comparison with the length of the original section of tubing, is greater. On the other hand, stretched tubing 18 now has a second wall thickness $T_2$ and a second inside diameter $ID_2$, as seen in FIG. 3, and both $T_2$ and $ID_2$ are less than the respective first wall thickness and inside diameter as provided in the original section of extruded tubing. It is appreciated that the stretching force is applied to the original extruded tubing not only in an amount to permanently deform the tubing but to arrive at the final desired dimensions. To this end, the original section of tubing is generally selected with a range of dimensions which can be changed to the final desired dimensions in accordance with the amount of force available to be applied. In the same vein, the means for applying the stretching force does not have to be any particularly designed device, but may be selected from many different type devices which are capable of imparting a longitudinal stretching force to a tubular product.

As a result of the applied stretching force, and after the final dimensions have been produced, the outside surface 19 of stretched tubing 18 has a different level of lubricity than the level on the original section of extruded tubing. This different level of lubricity has been found to be an improvement over the original level by measuring the same according to the friction force techniques as alluded to above. Typical friction force (surface lubricity) readings for extruded barium sulfate filled FEP tubing before stretching are: 1.0–3.5 oz. (28.3–99.1 g.); after stretching, the lubricity has been measured at: 0.5–0.8 oz. (14.2–22.6 g.). Thus, it can be seen that the post-extrusion operations of the present invention provide a smoother surfaced extruded thermoplastic tubing, with improved lubricity levels, thereby allowing the tubing to slide more freely and with less friction into the body of a patient.

The principles of stretching hollow extruded thermoplastic tubing are utilized most favorably in devices such as catheters in which the tubing portion thereof is inserted into the body of a patient. Depending upon fabrication techniques, the catheter tubing may generally be stretched to improve its surface lubricity either before or after the tubing is inserted into the hub in order to complete the catheter assembly, such as shown in FIG. 1. Whereas FIGS. 2–5 illustrate the stretching principles applied to just the tubing, FIGS. 6 and 7 illustrate the technique of stretching the catheter tubing of an already fabricated catheter assembly 20. Catheter assembly 20 includes a hub 21 which has a bore 22 therethrough, and a finite section of hollow extruded thermoplastic tubing 24 extending substantially axially from hub 21. Tubing 24, having been extruded in accordance with commonly known and standard extrusion processes, has a diameter $D_1$ and a length $L_3$; the diameter of the tubing is generally selected in order to be compatible with a mating insertion hole in hub 21, whereas length, $L_3$ is selected to provide a sufficiently long stretched length which may subsequently be trimmed, according to the desired final length of the catheter. In this condition, tubing 24, although relatively smooth from the standard extrusion process, has a first lubricity level on its peripheral surface.

Turning now to FIG. 7, a longitudinal stretching force F is applied to tubing 24 substantially along its longitudinal axis. Force F is of sufficient magnitude to exceed the elastic limit of the tubing to permanently stretch and deform the tubing. As a result of this stretching a second surface lubricity level on the outside surface of the tubing is produced, the second surface lubricity being an improvement over the first lubricity level. Accordingly, the catheter tubing may slide more freely into the body of the patient due to less surface friction and drag on the tubing.

Inasmuch as tubing 24 is already connected to hub 21, the stretching force generally causes a necking-down of the tubing at the point where it is connected to the hub. This necked-down portion can be controlled, for example, by applying a small amount of heat to only a portion of tubing 24. For instance, the portion 25 of the tubing adjacent hub 21 may be left unheated whereas the remaining portion 26, distally extending, is subject to the heating. As a result, when the longitudinal stretching force is applied, distal portion 26 will be stretched until a new diameter $D_2$ is formed being less than original diameter $D_1$; also, distal portion 26 has an increase in length designated as $L_4$. In addition, it is only distal portion 26 of the tubing which has a changed, surface lubricity on its outside surface. Proximal portion 25 generally retains the original diameter $D_1$ of the fabricated catheter assembly, while also retaining the original surface lubricity. The length $L_5$ of proximal portion 25 may be controlled according to the extent of heat application on the distal portion of the tubing. In most instances, distal portion 26 of the tubing is the major or substantial portion inasmuch as this section of the tubing will be leading the insertion of the catheter into the body of the patient. On the other hand, although proximal portion 25 of the tubing is the minor portion thereof, its larger diameter serves to provide a reinforcement of the catheter tubing with additional strength at the point where the tubing is connected to the catheter hub. This reinforced section, then, advantageously decreases the susceptibility of the tubing to bend at the point where it is connected to the hub.

In those embodiments where heat is applied to the catheter tubing in order to facilitate the stretching, it is preferable to heat the tubing, or a portion thereof, to a temperature above room temperature but below the melting point of the tubing. The heat application may be just prior to the stretching, or may be applied during the stretching.

It is also contemplated that, following the stretching operation, the catheter tubing will be trimmed to the desired length so that the catheter assembly may serve its proper function.

The invention will be further illustrated by the following specific example. It should be understood, however, that although this example may describe in particular detail some of the more specific features of this invention, it is primarily for purposes of illustration and the invention in its broader aspects is not to be construed as limited thereto.

EXAMPLE

An intravenous catheter assembly is prepared for fabrication. The catheter assembly has two separate components, a hub section and a hollow, elongate section of plastic tubing, the tubing prepared for mating insertion into the hub. The plastic tubing has been formed by an extrusion process and is made of barium sulfate filled FEP. As formed by the extrusion process, the tubing has an inside diameter of 0.038 inches (0.10 cm.) and a wall thickness of approximately 0.007 inches (0.018 cm.). At room temperature conditions, the tubing is passed through fresh pigskin mounted on a load cell of an Instron machine. The force required to advance the tubing through the pigskin is measured at 2.0 ounces (57 g.), which is a measure of the surface friction or lubricity of the tubing. By using an Instron machine equipped with jaws which grip the tubing, and using a mandrel having a diameter of 0.030 inches (0.076 cm.) over which the tubing is slid, a longitudinal stretching force is applied to the extruded tubing in order to substantially uniformly stretch the same. The amount of force applied is approximately 2.0 lbs. (0.91 kg.) and is sufficient to exceed the elastic limit of the tubing thereby permanently deforming the tubing. The stretching operation takes place when the tubing is substantially at room temperature, i.e., between 50° F. and 80° F. (10° C. and 26° C.). As a result of this stretching at these conditions, the stretched tubing now has an inside diameter of approximately 0.030 inches (0.076 cm.), which is approximately equivalent to the mandrel diameter, and a wall thickness of approximately 0.006 inches (0.015 cm.). Furthermore, the surface friction or lubricity measurement of the outside surface of the stretched tubing is now measured at 0.65 ounces (18.4 g.) using the same pigskin test as the pre-stretched tubing. Thus, with a lower level of surface and surface smoothness, the stretched tubing slides more freely and with less friction when inserted into the body. At this point, the stretched tubing may be trimmed to the desired length and is then inserted into the hub in order to complete fabrication of the intravenous catheter assembly.

Thus, there has been provided in accordance with the present invention a method of preparing extruded thermoplastic tubing for inclusion in medical devices in which the tubing is inserted into the human body and which has improved surface properties which will allow the tubing to more freely slide into the human body with less friction and concomitantly less patient discomfiture.

What is claimed is:

1. An intravenous catheter comprising a hub and a section of hollow, extruded, thermoplastic tubing made of a single uncoated material connected to said hub and extending substantially axially therefrom, said tubing having:
   a nonstretched portion extending a short distance from one end of said tubing, relative to the entire length of said tubing, and having a first outside diameter, a first inside diameter and a first surface lubricity;
   a stretched portion extending for the remainder of the length of said tubing and having a reduced outside diameter less than the outside diameter of said nonstretched portion and having a reduced inside diameter less than the inside diameter of the nonstretched portion and having a increased surface lubricity greater than the surface lubricity of the nonstretched portion so that said stretched portion of tubing may slide more freely and with less friction during intravenous insertion.

2. An intravenous catheter according to claim 1 wherein said second portion has been stretched to produce a second surface lubricity after the extrusion process for said thermoplastic tubing has been completed.

* * * * *